United States Patent [19]

Snow

[11] Patent Number: 4,557,262

[45] Date of Patent: Dec. 10, 1985

[54] DIALYSIS CLAMP

[76] Inventor: Kenneth T. Snow, P.O. Box 175, Gilberts, Ill. 60136

[21] Appl. No.: 580,335

[22] Filed: Feb. 15, 1984

[51] Int. Cl.⁴ .............................................. A61B 17/12
[52] U.S. Cl. .................................... 128/325; 128/346
[58] Field of Search ........... 128/324, 325, 346, 329 A, 128/327; 24/243 R

[56] References Cited

U.S. PATENT DOCUMENTS

| 2,754,825 | 7/1956 | Richmond | 128/327 |
| 3,147,754 | 9/1964 | Koessler | 128/325 |
| 3,884,240 | 5/1975 | Gilman | 128/346 |

*Primary Examiner*—Robert Peshock
*Attorney, Agent, or Firm*—Kenneth T. Snow

[57] ABSTRACT

This invention relates to a new and improved clamp for the "stick" holes of kidney dialysis patients when the needles are removed from the arm following treatment.

12 Claims, 5 Drawing Figures

U.S. Patent  Dec. 10, 1985  4,557,262
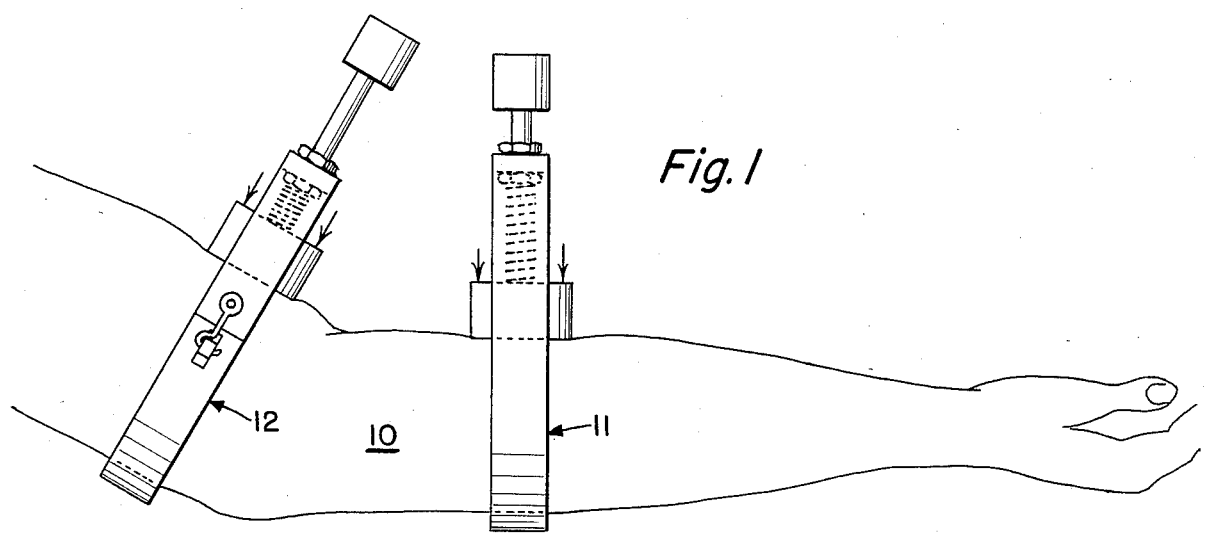
Fig. 1
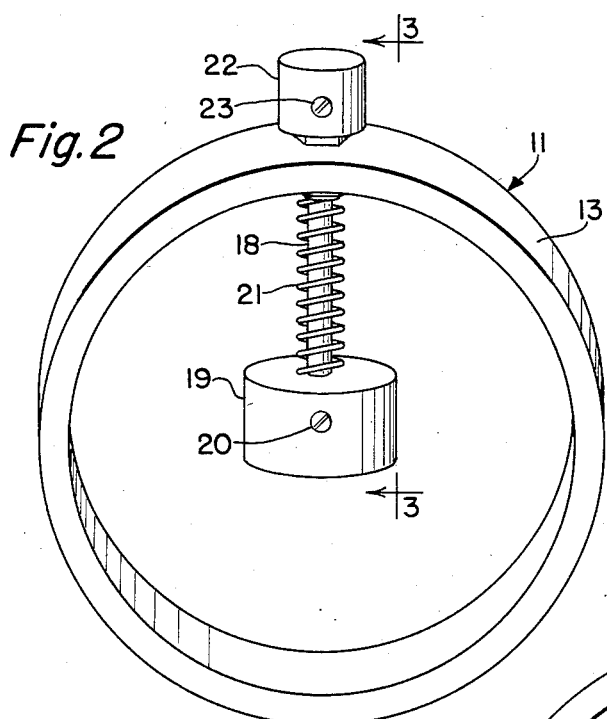
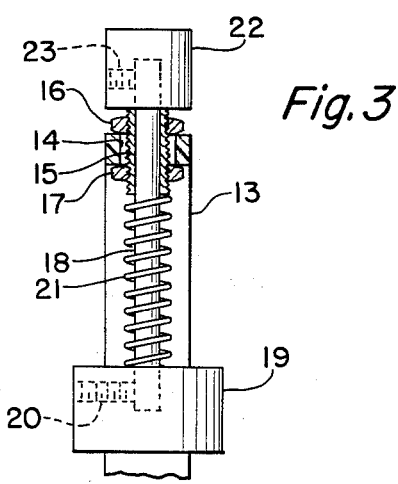
Fig. 2
Fig. 3
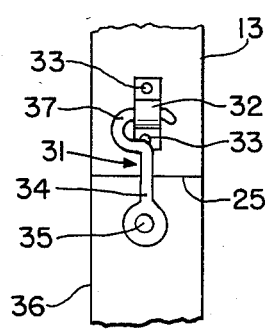
Fig. 5
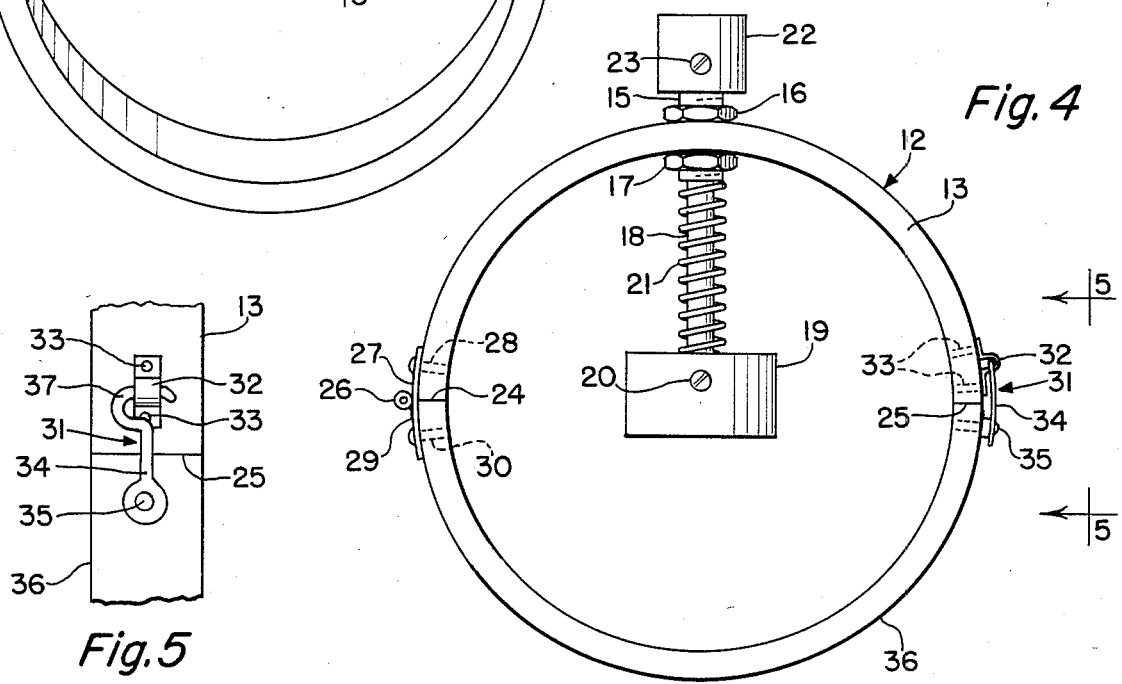
Fig. 4

DIALYSIS CLAMP

BACKGROUND OF THE INVENTION

1. Field of the Invention

Kidney dialysis patients have their blood removed and washed to clear it of impurities caused by non-function of the kidneys. This is normally accomplished by removing the blood from an artery in the arm and reinserting the washed blood into a vein in the same arm. The patients arm is preliminarily surgically treated to create a fistula or shunt between an artery and a vein. A needle is inserted into the artery from which blood is to be taken through flexible plastic tubes to the blood treating machine. A second needle is then inserted into the arm vein for the return of the dialyzed blood from the machine. The treatment lasts for several hours.

When the treatment is completed the needles are removed, one at a time and pressure must be applied to the needle hole to avoid the escapement of blood. As a rule a piece of gauze is placed on top of the needle hole and the patient asked to place his fingers in a firm grasp on the gauze cover. It usually takes from five to 15 minutes to cause the blood to coagulate and permit the gauze to be removed. The patients holding fingers tend to quiver and shake and cramp during the holding of the stick holes.

The mechanical clamp of the present invention is to be used in lieu of the finger holding. The clamp thus saves the patient the ordeal of holding his needle holes. It is preferred that two such clamps be used to cover both stick holes so that the needles may be removed substantially simultaneously and coagulation can be proceeding at both stick holes thus reducing overall coagulation time.

2. Description of the Prior Art

There is a clamp on the market to be used for dialysis. It is a scissors type of clamp, more like a spring biased clothespin. It has a number of deficiencies in that it exerts a pressure at an acute angle relative to the patient's arm rather than a direct vertical pressure which is more effective. Also, the prior clothespin type of clamp is fragile and tends to break down easily during use and further is prohibitive in cost.

SUMMARY OF THE INVENTION

The clamp of this invention comprises a rigid cylindrical support or base, preferably made of plastic. The cylindrical base is sufficiently large in diameter to permit it to be loosely slid over the arm of a dialysis patient. This circular base constitutes a relatively short cylinder. A hole is provided radially through the wall of the cylinder. A rod is adapted to slide radially through the hole to a position within the cylinder base support. Bushing means is provided in the cylinder radial hole. A short rod is adapted to slidably engage the bushing for radial movement into and out of the cylinder. A pressure pad is removably affixed to the inner end of the rod within the cylinder. A spring surrounds the rod between the inner surface of the cylinder and the pressure pad to thereby urge the pressure pad radially inwardly and the supporting ring in a direction away from the arm. The spring thus performs the dual function of holding the cylindrical support firmly against the back side of the patient's arm and spring urges the pressure pad against the needle hole in the front side of the arm. A hand engaging knob is removably affixed to the end of the rod extending outwardly of the circular support.

The outer knob permits the user to manually retract the pressure pad against the action of the spring.

Thus when dialysis is completed and one of the sticks is removed a pad of gauze is placed over the stick hole and the clamp of this invention allowed to hold the gauze until the blood coagulates.

A modified form of the dialysis clamp is to provide the cylindrical base with a hinged lower half. The lower half of the ring is cut through and hinged at one side and removably fastened by an openable and closable latch at the other side. This permits the clamp to be easily removed sidewise from the patient's arm rather than having to slide the clamp over the arm and the hand of the patient as well as over plastic tubes which may still be present.

IN THE DRAWINGS

FIG. 1 is a side view of a patient's arm with the pressure clamps of this invention mounted thereon.

FIG. 2 is a perspective view of the pressure clamp of this invention.

FIG. 3 is a sectional view of the device as taken on the line 3—3 of FIG. 2.

FIG. 4 is a front elevational view of a modified form of the pressure clamp of this invention.

FIG. 5 is a front elevational view of the latch member of the clamp 12 and as taken on the line 5—5 of FIG. 4.

AS SHOWN IN THE DRAWINGS

The reference numeral 10 indicates generally the arm of a kidney dialysis patient. In most instances the treatment of a patient's blood occurs in the arm but in some patients the treatment is given in the leg and it should be understood that the numeral 10 is intended to be either the arm or leg and in some points in this description reference is made to the limb of the patient.

When one starts kidney dialysis the arm is operated on and an artery is surgically attached to a vein to produce a "fistula" or "shunt." Dialysis treatment is made in the arm containing the shunt. One needle is inserted into the artery. Plastic tubing joins the needle to the blood treating machine. The patient's blood is withdrawn through this artery inserted needle and delivered to the dialyzing machine. The machine washes and treats the blood. A second needle is inserted into the vein in the patient's arm. The needles are a short distance apart, usually about 2 to 3 inches. It is through the second needle by means of further plastic tubing that the washed and treated blood is returned to the patient's body. The plastic tubing is preferably taped to the patient's arm in a looped fashion to prevent direct pulling on the functioning needles.

FIG. 1 depicts a first dialysis clamp 11 covering the artery needle hole or stick point as it is referred to at dialysis clinics. A second dialysis clamp 12 is mounted on the patient's arm at a position spaced from the first clamp. This second clamp 12 is used to apply pressure to the vein needle hole after that needle is withdrawn at the end of treatment.

Following removal of the needles the patient's blood continues to spurt out from these holes unless pressure is applied to these openings. In time the blood coagulates and pressure is removed. As stated earlier, the attending nurse applies a pad of folded gauze onto the stick holes and then it becomes the patient's job to tightly hold the gauze pad with his other hand. Obviously only one stick point may be held by the patient at one time. Holding the gauze pad is a tedious job and in no time at all the patient's hand tends to give out and it seems forever for the blood to clot and thus close the stick hole. Then the operation is repeated on the second stick hole and the patient is asked to hold that hole until the blood coagulates. This constitutes a long procedure very disconcerting to the patient. The clamps of the present invention are used in place of the patient's manual pressure thus greatly alleviating the patient's anxiety for his blood to coagulate.

As best shown in FIG. 2 the clamp 11 is equipped with a rigid plastic ring 13 in the form of a short cylinder. The cylinder 13 is sufficiently large in diameter to loosely slide over a patient's arm. This diameter is in the range of 4½ inches. The length of the cylinder is preferably in the order of ¾ inches long but could be shorter or longer as desired. The back or underside surface of the cylinder 13 abuts the backside of the patient's arm and it is desired that the length of the cylinder be such as not to cut into the patient's arm.

A radially disposed hole 14 is cut through the cylinder 13 at a position midway of the length of the cylinder. In order to insure proper guiding of the clamp a bushing 15 is inserted radially through the hole 14 and is locked in position on the cylinder by a lock nut 16 on the outer surface of the cylinder 13 and a second lock nut 17 threadedly engaging the bushing 15 and abutting the inside of the cylinder 13. The lock nuts 16 and 17 act to secure the bushing 15 firmly to the cylindrical base 13 and to hold it in a true radial position. The bushing 15 is externally threaded in opposite directions so that the lock nuts may be drawn up tightly against the outer and inner surfaces of the cylinder.

A rod 18 is employed to slidably engage the radial hole of the bushing 15. The diameter of the rod is just slightly less than the radially disposed bushing opening and thus there is a snug fit therebetween, but sufficient room to permit free sliding of the rod within the bushing. The rod is constantly in a radial position within the cylindrical housing 13.

A pressure pad 19 is affixed to the internal end of the rod 18. The pad is preferably circular in shape but will effectively work to seal off a needle hole regardless of shape. Here the pressure pad has a flat lower surface to thereby press against the patient's arm and to give the blood time to coagulate and thus close off the needle hole. A set screw 20 threadedly engages the side of the pressure pad 19 and is adapted to be moved inwardly for engagement with the side of the rod 18.

A spring 21 surrounds the rod between the pressure pad 19 and the inside wall of the cylindrical housing 13. The spring 21 thus performs the dual function of urging the pressure pad 19 in a true radial push against the front surface of the patient's arm and simultaneously pulls the under or back side of the cylindrical housing against the underside of the patient's arm. Thus the clamp is firmly affixed to the patient's arm by gripping both sides thereof in a direct radial path.

A knob 22 is mounted on the outer end of the rod 18 outside the cylinder housing 13. A set screw 23 carried in the side of the knob 22 is adapted to be turned inwardly toward the rod to abuttingly engage the rod and hold the knob to the rod. The knob is employed as a hand gripping means to retract the pressure pad and its spring during application to and removal from the patient's arm.

THE OPERATION OF THE DIALYSIS CLAMP

Following treatment for dialysis the needles for removing and reinserting the blood are removed and must have pressure applied over these needle stick holes to give the blood an opportunity to coagulate and thus close off those holes without bleeding. The cylindrical housing 13 with the hand knob manually pulled outwardly is drawn over the hand and the arm of the patient to a position over one of the needle holes. At this point the hand knob is released causing the pressure pad to be spring biased against the top side of the arm where the needle was withdrawn. The backside of the cylindrical housing 13 is spring pulled against the backside of the patient's arm to thereby hold the clamp in fixed position on the arm with no other manual help. This is shown in FIG. 1 of the drawings.

FIGS. 4 and 5 show the clamp with the modification of having the lower half of the cylinder 13 mounted for hinged relationship with the upper half which carries the radial rod and its spring biased pressure pad. This is accomplished by cutting through the cylinder wall at 24 and again at 25 which is diametrically opposite the first cut 24. A hinge 26 is mounted on the cylinder 13 at the location of the first cut 24. The upper half 27 of the hinge is fastened by bolts or rivets shown at 28 to the upper half of the cylinder 13. A lower hinge part 29 is fastened by means of bolts or rivets 30 to the lower half of the cylinder 13.

A latch means 31 is arranged to hold closed or open the upper and lower parts of the cylinder 13 defined by the cut 25. A first or fixed latch part 32 is affixed by means of bolts or rivets 33 to the upper half of the cylinder 13. A complementary latch part 34 is affixed by a swivel pin 35 to the lower half of the cylinder 13 designated by the numeral 36. The complementary latch part 34 is adapted to be swung about its swivel connection at pin 35 and with a hook 37 formed at its outer end is engaged or disengaged with the first latch part 32. When the latch is disengaged the cylindrical housing 13 is adapted for mounting over the side of the patient's arm rather than having to slide the clamp over the length of the patient's arm. When the pressure pad of the clamp 12 is located over the needle hole the lower half 36 of the cylinder 13 is swung upwardly about its hinge 26 and the diametrically disposed latch 31 has its complementary elements reunited thus closing the cylinder and making it operate in exactly the same manner as the clamp 11. For side removal of the clamp 12 the latch is disconnected permitting the lower half 36 of the cylinder to drop away and the clamp easily removed from the side of the patient's arm.

I am aware that numerous details of construction may be made throughout a wide range without departing from the principles shown herein and I do not propose limiting the patent granted hereon otherwise than as necessitated by the appended claims.

What is claimed is:

1. A clamp for kidney dialysis patients comprising a short cylindrical housing of rigid plastic material, said cylindrical housing having a radial hole in one side thereof, a radially slidable rod passing through said cylindrical housing hole, means guiding said rod for true radial movement into said cylindrical housing through said hole, a pressure pad affixed to the inner end of said rod, spring means mounted around said rod and disposed between the pressure pad and the inner surface of the cylindrical housing, means manually slidably withdrawing said rod with its pressure pad outwardly to compress the spring and permit the clamp to be slid over a patient's arm to the desired point of pressure.

2. A clamp as set forth in claim 1 in which said means for manually withdrawing the rod and its spring means comprising a hand engaging knob on the rod positioned externally of the cylindrical housing.

3. A device as set forth in claim 1 in which the lower half of the cylindrical housing has means for separably fastening it to the upper half of said cylindrical housing.

4. A device as set forth in claim 3 in which one side of said lower half of said cylindrical housing is hinged to the upper half of the cylindrical housing and the other side is equipped with removably attachable latch means for joining or separating the lower half from the upper half.

5. A cylindrical base ring of short length and of a diameter to loosely fit over the arm of a dialysis patient, a radial hole in the wall of the cylindrical ring, a radial bushing locked within the radial hole, a rod adapted to slidably engage the bushing and move in a radial path within and without the cylindrical base ring, said bushing adapted to guide said rod in its radially movable path, a pressure pad affixed to the inner end of said rod, a manual engaging handle affixed to the outer end of said rod, a spring surrounding said rod between the pressure pad and the inner surface of said cylindrical ring base adjacent the radially disposed bushing, said spring acting to pull the lower half of the cylindrical ring base against the underside of a patient's arm and to radially urge said pressure pad against the top side of the patient's arm at the position of the needle withdrawal.

6. A pressure clamp for stopping the flow of blood from a patient's arm or leg to give a wound an opportunity for the blood to coagulate comprising a cylindrical base member utilized to encircle a patient's limb, said cylindrical base member having a radial hole through its outer wall, a rod adapted to slide radially through said hole, a pressure pad mounted on the inner end of said rod within said cylindrical base member, a spring surrounding said rod and disposed between the pressure pad and the inner surface of said cylindrical base member and adapted to urge said pressure pad radially inwardly against the front side of a patient's limb and to simultaneously firmly hold the cylindrical base member against the back side of the patient's limb, a handle affixed to the end of the rod on the outside of the cylindrical housing to permit manual retraction of the pressure pad.

7. A device as set forth in claim 6 in which the cylindrical base member has means removably fastening the lower half to the upper half thereof.

8. A device as set forth in claim 7 in which said means removably fastening comprises a hinge on one side and a removably fastening latch means at the side diametrically opposite the hinge.

9. A dialysis clamp for the stick holes of needles after they are withdrawn following dialysis treatment comprising a relatively large diameter plastic ring base, said plastic ring base being made of relatively rigid plastic, said ring divided into upper and lower halves, means joining said upper and lower halves, the top center of the upper half having a radial hole therein, a rod slidably radially through said upper half hole, a pressure pad affixed to the inner end of said rod, a spring surrounding said rod and positioned between said pressure pad and the inside of the plastic ring base, and hand engaging means on said rod on the outside of the plastic ring base whereby the spring acts to hold the plastic ring to the arm of a patient and to exert a constant pressure to the needle hole in the patient's arm.

10. A device as set forth in claim 9 in which the means joining the lower half of the plastic ring base to the upper half thereof comprises a hinge at one side and removably attachable latch means at the diametrically opposite side.

11. A clamp for closing off the flow of blood from the arm of a patient who has had a needle removed therefrom, comprising a housing having a circular lower portion adapted to engage the underside of the arm, said housing having an upper circular portion adapted for positioning over the top side of the arm from which the needle has been removed, means rigidly connecting said lower and upper circular portion of the housing, the upper portion of said housing having a radial hole therein, a rod, means guiding the rod for vertical sliding movement through said hole, a pressure pad affixed to the inner end of the rod, a spring surrounding said rod and positioned between said pressure pad and the inner surface of said upper portion of said housing, and hand engaging means affixed to the rod externally of said upper housing portion for manually retracting said pressure pad against the action of the spring.

12. A clamp for closing off the flow of blood from the arm of a patient who has had a needle removed therefrom, comprising a housing having a circular lower portion adapted to engage the underside of the arm, said housing having an upper circular portion adapted for positioning over the top side of the arm from which the needle has been removed, means rigidly connecting said lower and upper circular portion of the housing, the upper portion of said housing having a radial hole therein, a rod, means guiding the rod for vertical sliding movement through said hole, a pressure pad affixed to the inner end of the rod, a spring surrounding said rod and positioned between said pressure pad and the inner surface of said upper portion of said housing, and means associated with said pressure pad and said slidable rod for effecting manual raising of said pressure pad and said rod against the action of the spring and moving them out of contact with the dialysis patients arm which received the dialysis treatment.

* * * * *